US006399374B1

(12) United States Patent
Vogelstein et al.

(10) Patent No.: US 6,399,374 B1
(45) Date of Patent: Jun. 4, 2002

(54) CONVERTING DIPLOIDY TO HAPLOIDY FOR GENETIC DIAGNOSIS

(75) Inventors: Bert Vogelstein, Baltimore; Kenneth W. Kinzler, BelAir; Hai Yan, Baltimore, all of MD (US); Nicholas Papadopoulos, New York, NY (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/461,047

(22) Filed: Dec. 15, 1999

Related U.S. Application Data
(60) Provisional application No. 60/158,160, filed on Oct. 8, 1999.

(51) Int. Cl.[7] .................................. C12N 5/12
(52) U.S. Cl. ....................................... 435/346
(58) Field of Search ................ 435/6, 449, 455, 435/346

(56) References Cited

U.S. PATENT DOCUMENTS

| | | | |
|---|---|---|---|
| 5,288,625 A | * | 2/1994 | Hadlaczky .................. 435/440 |
| 5,612,201 A | | 3/1997 | De Plaen et al. |
| 5,721,118 A | * | 2/1998 | Scheffler .................... 435/69.1 |
| 6,063,375 A | * | 5/2000 | Gattoni-Celli et al. ... 424/93.21 |
| 6,077,697 A | * | 6/2000 | Hadzlaczky et al. ......... 435/440 |

FOREIGN PATENT DOCUMENTS

| | | | | |
|---|---|---|---|---|
| WO | WO 98/08964 | * | 3/1998 | ............... 435/455 |

OTHER PUBLICATIONS

Pietenpol et al. Mammalian cells resistant to tumor suppressor genes. PNAS vol. 93:8390–8394, Aug. 1996.*

Tindall et al. Complementation of mismatch repair gene defects by chromosome transfer. Mutation Res. vol. 402:15–22, Jan. 1998.*

Nyormoi et al. Proliferating hybrid cells froed between rat spematids and an established line of mouse fibroblasts. J. Cell Sci. vol. 13:863–878, Dec. 1973.*

Tolsma et al. Transformation of NIH/3T3 to anchorage independence by H–Ras is accompanied by loss of suppressor activity. Exp. Cell Res. vol. 205:232–239, Jun. 1993.*

McDaniel et al. Confirmation of homozygosity for a single nucleotide substitution mutation in a cockayne syndrome patient using monoallelic mutation analysis in somatic cell hybrids. Human Mutation vol. 10:317–321, May 1997.*

Kayes et al. Deletion spanning the neurofibromatosis I gene: Identification and phenotype of five patients. Am. J. Hum. Genet. vol. 54:424–436, May 1994.*

Pazzaglia et al. "Somatic Cell Hybrids for High–Density Mapping of Chromosome 2 Breakpoints in Radiation–Induced Myeloid Leukemia Cell Lines from Inbred Mice" Molecular Carcinogenesis 27:219–228 (2000).

McDaniel et al. "Confirmation of Homozygosity for a Single Nucleotide Substitution Mutation in a Cockayne Syndrome Patient Using Monoallelic Mutation Analysis in Somatic Cell Hybrids" Human Mutation 10:317–321 (1997).

PCT International Search Report, PCT/US00/27508.

Leach, F.S. et al.; "Mutations of the Muts Homolog In Heredity Nonpolyposis Colorectal Cancer"; Cell Press, vol. 75, No. 6, Dec. 1993, pp. 1215–1225.

Hosoi, E. et al.; "A Human–Mouse Hybrid Cell Line Expressing Both Human Leukocyte and Histocompatibility–2 Antigens", Japanese Journal of Physiology, vol. 40, No. 1, 1990, pp. 297–304.

Yan, et al.; "Conversion of Diploidy to Hapliody", Nature (London), vol. 403, No. 6771, Feb. 2000, pp. 723–724.

* cited by examiner

Primary Examiner—Remy Yucel
Assistant Examiner—William Sandals
(74) Attorney, Agent, or Firm—Banner & Witcoff Ltd.

(57) ABSTRACT

Detection of mutations associated with hereditary diseases is complicated by the diploid nature of human cells. Mutations present in one allele are often masked by the wild-type sequence of the other allele. Individual alleles can be isolated from every chromosome within somatic cell hybrids generated from a single fusion. Nucleic acids from the hybrids can be analyzed for mutations in an unambiguous manner. This approach was used to detect two cancer-causing mutations that had previously defied genetic diagnosis. One of the families studied, Warthin Family G, was the first kindred with a hereditary colon cancer syndrome described in the biomedical literature.

16 Claims, 4 Drawing Sheets

Hybrid 1

Donor

Hybrid 3

Hybrid 1

Donor

Hybrid 3

US 6,399,374 B1

CONVERTING DIPLOIDY TO HAPLOIDY FOR GENETIC DIAGNOSIS

This application claims the benefit of provisional application Ser. No. 60/158,160 filed Oct. 8, 1999.

This invention was supported with U.S. government funds, NIH grants CA43460, CA57345, CA62924, CA67409, CA72851. The government therefore retains certain rights in the invention.

BACKGROUND OF THE INVENTION

The problem with humans, at least from a genetic diagnostic perspective, is that they are diploid. Mutations in one allele, such as those responsible for all dominantly inherited syndromes, are always accompanied by the wild-type sequence of the second allele. Though many powerful techniques for genetic diagnosis have been developed over the past decade, all are compromised by the presence of diploidy in the template. For example, the presence of a wild-type band of the same electrophoretic mobility as a mutant band can complicate interpretation of sequencing ladders, especially when the mutant band is of lower intensity. Deletions of a segment of DNA are even more problematic, as in such cases only the wild-type allele is amplified and analyzed by standard techniques. These issues present difficulties for the diagnosis of monogenic diseases and are even more problematic for multigenic diseases, where causative mutations can occur in any of several different genes. Such multigenism is the rule rather than the exception for common predisposition syndromes, such as those associated with breast and colon cancer, blindness, and hematologic, neurological, and cardiovascular diseases. The sensitivity of genetic diagnostics for these diseases is currently suboptimal, with 30% to 70% of cases refractory to genetic analysis.

There is a need in the art for simply separating and analyzing individual alleles from human cells.

SUMMARY OF THE INVENTION

It is an object of the invention to provide a method for detecting mutations in a gene of interest on a human chromosome.

It is another object of the invention to provide a method for making test cells suitable for sensitive genetic testing.

It is yet another object of the invention to provide a population of fused cell hybrids which are useful for genetic analysis.

These and other objects of the invention are provided by one or more of the embodiments described below. In one embodiment a method of detecting mutations in a gene of interest of a human is provided. Cells of a human are fused to rodent cell recipients to form human-rodent cell hybrids. Fused cell hybrids are selected by selecting for a first marker contained on a rodent chromosome and for a second marker contained on a first human chromosome, forming a population of fused cell hybrids. A subset of hybrids are detected among the population of fused cell hybrids. The hybrids are haploid for a second human chromosome which is not the same chromosome as the first human chromosome and which was not selected. The subset of hybrids are tested to detect a gene, an mRNA product of said gene, or a protein product of said gene. The gene resides on the second human chromosome. Diminished amounts of the mRNA or protein product or altered properties of the gene, mRNA, or protein product indicate the presence of a mutation in the gene in the human.

According to another embodiment, a method is disclosed which provides test cells for genetic testing. The test cells are haploid for human genes. Cells of a human are fused to transformed, diploid, rodent cell recipients to form human-rodent cell hybrids. Fused cell hybrids are selected by selecting for a marker on each of a first human chromosome and a rodent chromosome, forming a population of cells which stably maintain one or more human chromosomes in the absence of selection for the human chromosomes. Cells which are haploid for a second human chromosome which is distinct from the first human chromosome are detected among the population of cells; the second human chromosome was not selected.

Also provided by the present invention is a population of rodent-human hybrid cells wherein each homolog of at least 2 human autosomes is present in haploid form in at least one out of one hundred of the cells.

The present invention thus provides the art with a method which can be used to increase the sensitivity and effectiveness of various diagnostic and analytic methods by providing hybrid cells to analyze which are haploid for one or more genes of interest. The human chromosome content of the hybrid cells is stable and uniform.

BRIEF DESCRIPTION OF THE DRAWINGS

(FIG. 2A) Polymorphic markers from the indicated chromosomes were used to determine the genotype of the indicated hybrids. "Donor" denotes the human lymphocytes used for fusion with the mouse recipient cells. (FIG. 2B) cDNA of E2 and four hybrids were used as templates to amplify hMSH2, hMSH6, hMLH1, hTGF β-RII, hPMS1, hPMS2, and APC sequences. The results were concordant with the genotypes observed in (FIG. 2A), in that hybrids 5–7 retained at least one allele of each of the chromosomes containing the tested genes, while hybrid 8 contained alleles of chromosomes 3, 5, and 7 but not of chromosome 2 (containing the hMSH2, hPMS1, and hMSH6 genes).

(FIG. 3C) Sequences representing the indicated exons of hMSH2 were amplified from the indicated hybrids. Exons 1–6 were not present in the hybrids containing allele A, but exons 7–16 were present in hybrids containing either allele.

(FIG. 4A) Sequence analysis of RT-PCR products from hMSH2 transcripts of hybrid 1, containing the mutant allele of a Warthin family G patient, illustrates a 24 bp insertion (underlined; antisense primer used for sequencing). The wild-type sequence was found in hybrid 3, containing the wt allele. RT-PCR analysis of transcripts from lymphoid cells of the patient showed that the mutant transcript was expressed at significantly lower levels than the wild-type sequence. Sequence analysis of the genomic DNA of the same hybrids (FIG. 4B) showed that the insertion was due to a A to C mutation (antisense sequence, indicated in bold and underlined) at the splice acceptor site of exon 4, resulting in the use of a cryptic splice site 24 bp upstream. The signal of the mutant C is not as strong as the wild-type A in the donor's DNA. Such non-equivalence is not unusual in sequencing templates from diploid cells, and can result in difficulties in interpretation of the chromatograms. (FIG. 4C) Extracts from hybrids 1 and 5, carrying the mutant allele of chromosome 2, were devoid of hMSH2 protein, while extracts of hybrids 2 and 3, carrying the wt allele, contained hMSH2 protein. Hybrid 4 did not contain either allele of chromosome 2. Hybrids 1, 3, 4, and 5 each carried at least one allele of chromosome 3 and all synthesized hMLH1 protein. α-tubulin served as a protein loading control. Immunoblots with antibodies to the indicated proteins are shown.

DETAILED DESCRIPTION OF THE PREFERRED EMBODIMENTS

Figure 1:
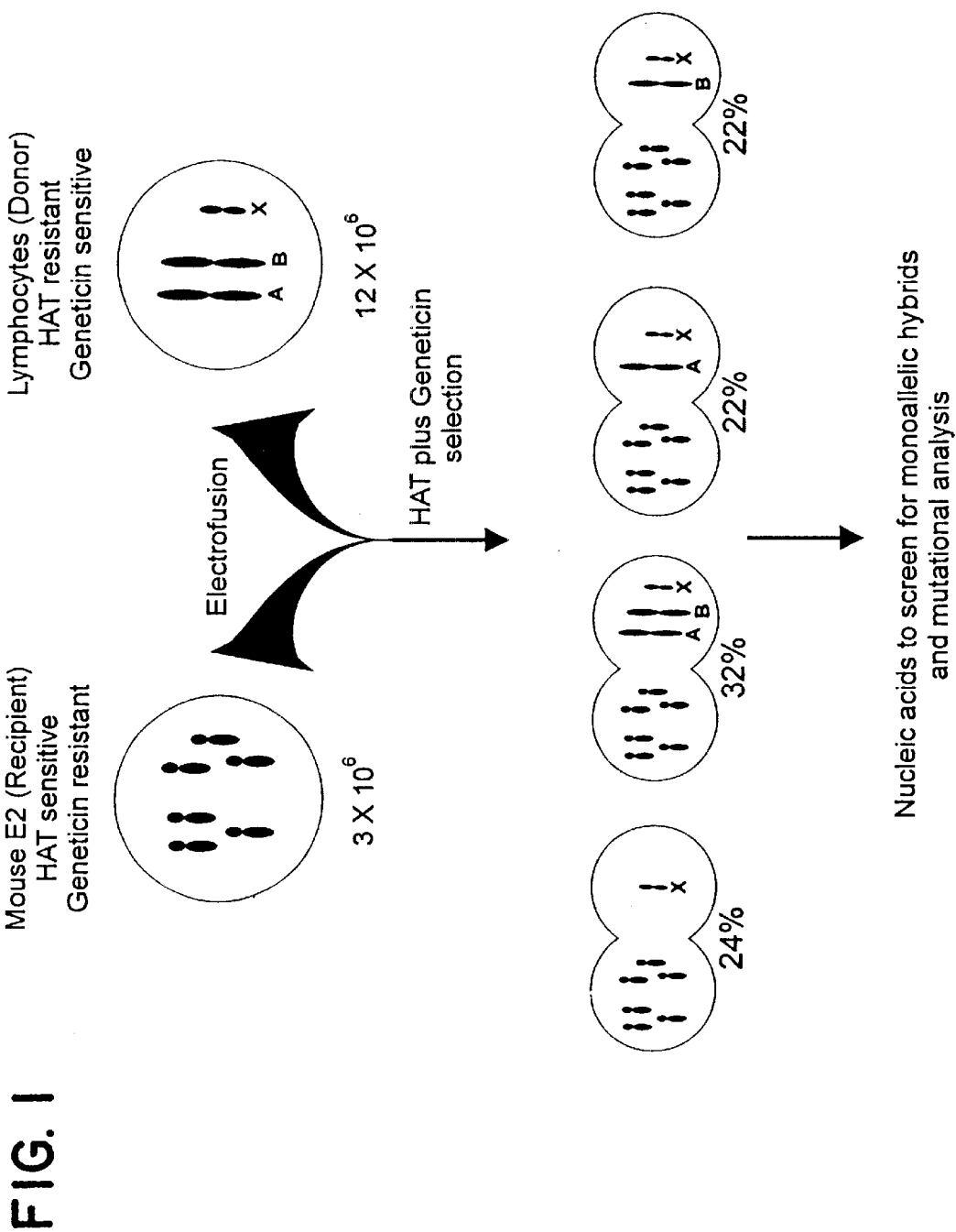
FIG. 1. Strategy for hybrid generation. The recipient mouse cell line E2 was fused with human lymphocytes and clones were subsequently selected with HAT plus geneticin, which kill unfused E2 cells and lymphocytes, respectively. All clones contained a human X chromosome responsible for growth in HAT. Clones were genotyped to determine which human chromosomes were retained. Chromosomes marked "A" and "B" represent the two homologs of a representative human chromosome. The average proportion of clones which retained neither, both, or either of the six chromosome homologs analyzed is indicated (see text). Mutational analysis was carried out on nucleic acids of clones which retained single alleles of the genes to be tested.

We have devised a strategy for generating hybrids containing any desired human chromosome using a single fusion and selection condition. Importantly and unexpectedly, the human chromosomes in these hybrids were stable, and they expressed human genes at levels sufficient for detailed analysis. The approach is based on the principle that fusion between human and rodent cells creates hybrid cells that contain the full rodent genomic complement but only a portion of the human chromosomes. In the past, selection for retention of a specific human chromosome (by complementation of an auxotrophic rodent cell, for example) has allowed the isolation of hybrids containing a desired chromosome (7, 8). Though such fusions have proven useful for a variety of purposes (8, 9), their utility has been limited by the availability of appropriate rodent recipients for many chromosomes and by the inefficiencies and variation of the fusion and selection conditions. For the analysis of multigenic diseases, it would be necessary to perform a separate fusion and selection for each chromosome.

The stability of the human chromosomes in the hybrids of the present invention was surprising. Though the human genetic constitution of radiation hybrids is relatively stable, this stability has been presumed to be due to the integration of small pieces of human DNA into rodent chromosomes following irradiation of the donor cells. The human chromosomes in whole cell fusions have been believed to be unstable unless continuous selection pressure for individual chromosomes was exerted. The reasons for the stability in our experiments is unclear, but may be related to the diploid nature of the rodent partner. Such diploidy reflects a chromosome stability that is unusual among transformed rodent cells. Previous experiments have indeed shown that chromosomally stable human cells retain all chromosomes upon fusion with other chromosomally stable human cells, unlike the situation when one of the two partners is chromosomally unstable.

The diploid, rodent recipient cells of the present invention provide useful reagents for the facile creation of cells with functionally haploid human genomes. Nucleic acids or proteins from these hybrids can be used as reagents for any standard mutational assay. As mutational assays are constantly being improved and automated (1), the value of the hybrid-generated materials correspondingly increases. It may soon become possible, in fact, to examine the sequence of entire genes (promoters and introns in addition to exons). Nucleic acid templates generated from single alleles are clearly superior for such analyses, as the homogeneous nature of the templates dramatically enhances the signal to noise ratio of virtually any diagnostic assay. We therefore envision that this approach can be productively applied to a wide variety of research and clinical problems.

Genes of interest are typically those which have been found to be involved in inherited diseases. These include genes involved in colon cancer, breast cancer, Li-Fraumeni disease, cystic fibrosis, neurofibromatosis type 2, von Hippel-Lindau disease, as well as others. The identified genes include APC, merlin, CF, VHL, hMSH2, p53, hPMS2, hMLH1, BRAC1, as well as others. Mutations which can be identified at the protein level include those in sequences that regulate transcription or translation, nonsense mutations, splice site alterations, translocations, deletions, and insertions, or any other changes that result in substantial reduction of the full-length protein. Other subtler mutations can be detected at the nucleic acid level, such as by sequencing of RT-PCR products.

Cells of the human which may be used in fusions are any which can be readily fused to rodent cells. Peripheral blood lymphocytes (PBL) which are readily available clinical specimens are good fusion partners, with or without prior mitogenetic stimulation, whether used fresh or stored for over one year at −80° C. Since inherited mutations are the subject of the present method, any cells of the human body can be used, since all such cells contain essentially the same genetic complement.

Rodent cell recipients for fusion are preferably diploid, more preferably oncogene-transformed, and even more preferably have microsatellite instability due to a defect in a mismatch repair gene. Selection of particular clones which grow robustly, are stably diploid, and fuse at a high rate is well within the skill of the ordinary artisan.

Fusion of cells according to the present invention can be accomplished according to any means known in the art. Known techniques for inducing fusion include polyethylene glycol-mediated fusion, Sendai virus-mediated fusion, and electro-fusion. Cells can desirably be mixed at a ratio of between 10:1 and 1:10 human to rodent. Clones of fused cells generally become visible after about two to three weeks of growth.

Fused hybrid cells can be selected using any markers which result in a positively selectable phenotype. These include antibiotic resistance genes, toxic metabolite resistance genes, prototrophic markers, etc. The surprising advantage of the present invention is that a single marker on a single human chromosome can be used in the selection, and that stable hybrids containing more than just the single, selected human chromosome result. Thus markers on other chromosomes can be analyzed even when the chromosomes on which the markers reside were not selected.

Fused hybrid cells can be analyzed to determine that they do in fact carry a human chromosome. which carries a gene of interest. Hybrid cells which have either of the two relevant human chromosomes can be distinguished from each other as well as from hybrids which contain both of the two human chromosomes. See FIG. 1. While any means known in the art for identifying the human chromosomes can be used, a facile analysis can be performed by assessing microsatellite markers on the human chromosome. Other linked polymorphic markers can be used to identify a desired human chromosome in the hybrids.

Once hybrid cells are isolated which contain one copy of a human gene of interest from a human who is being tested, mutation analysis can be performed on the hybrid cells. The genes can be tested directly for mutations, or alternatively the mRNA or protein products of the genes can be tested. Mutations that result in reduced expression of the full-length gene product should be detectable by Western blotting using appropriate antibodies. Tests which rely on the function of the protein encoded by the gene of interest and enzyme assays can also be performed to detect mutations. Other immunological techniques can also be employed, as are known in the art.

If an immunological method is used to detect the protein product of the gene of interest in the hybrids, it is desirable that antibodies be used that do not cross-react with rodent proteins. Alternatively, the rodent genes which are homologous to the gene of interest can be inactivated by mutation to simplify the analysis of protein products. Such mutations can be achieved by targeted mutagenesis methods, as is well known in the art.

Functional tests can also be used to assess the normalcy of each allelic product. For example, if one inserted an expression construct comprising a β-galactosidase gene downstream from a p53 transcriptional activation site, into a rodent-human hybrid cell that contained human chromosome 17 but no endogenous p53, then one could detect mutations of the p53 on the human chromosome 17 by staining clones with X-gal. Other enzymatic or functional assays can be designed specifically tailored to the gene of interest.

Any method of detecting mutations at the DNA or RNA level as are known in the art may be employed. These include without limitation, sequencing, allele-specific PCR, allele-specific hybridization, microarrays, DGGE, and automated sequencing.

It is a possibility that expression of the gene of interest might be inhibited in the hybrid cell environment. In order for the loss of expression of a gene of interest in the hybrid cells to be meaningfully interpreted as indicating a mutation in the human, one must confirm that the gene of interest, when wild-type, is expressed in rodent-human hybrid cells. This confirmation need not be done for each patient, but can be done once when the assay is being established.

When the assay of the present invention indicates that a mutation exists in the gene of interest, other family members can be tested to ascertain whether they too carry the mutation. Alternatively, the other family members can be tested to see if they carry the same chromosome as the affected family member. This can be determined by testing for a haplotype, i.e., a set of distinctive markers which are found on the chromosome carrying the mutation in the affected family member. Determination of a haplotype is a by-product of performing the assay of the invention on the first family member. When the hybrid cells are tested to confirm the presence of the relevant chromosome in the hybrid, for example by use of microsatellite markers, a distinctive marker set will be identified, which can then be used as a haplotype.

Mixed populations of hybrid cells made by the fusion process of the present invention may contain hybrid cells which are haploid for a number of different human chromosomes. Typically each homolog of at least 2, at least 5, at least 10, at least 15, at least 20, or even 22 human autosomes will be present in the population in a haploid condition in at least one out of one hundred, seventy-five, fifty, thirty or twenty-eight of the cells. Thus a high proportion of the cells contain multiple human chromosomes, and a relatively small number of cells must be tested to find cells harboring a single copy of a non-selected chromosome.

Populations of cells resulting from a single hybrid are uniform and homogeneous due to the high stability of the human chromosomes in the hybrid cells of the invention. Thus at least 75%, 80%, 85%, 90%, 95%, 97%, 99%, or 100% of the cells in the population resulting from a single hybrid cell contain the same complement of human chromosomes.

The following examples provide experimental details which demonstrate one of many ways to carry out the invention. The invention is not limited to the particular methods of cells employed in the examples. The claims and the specification as a whole provide the measure of the invention.

EXAMPLES

Example 1

An outline of the approach is presented in FIG. 1. The rodent fusion partner was a line derived from mouse embryonic fibroblasts transformed with ras and adenovirus E1A oncogenes. HPRT-deficient subclones of this line were generated, and one subclone (E2) was chosen for further experimentation based on its robust growth characteristics, maintenance of diploidy, and fusion efficiency (10). Human lymphocytes cells were mixed with E2 cells at an optimum ratio and electrofused, and hybrids selected in geneticin (to kill unfused human cells) and HAT (to kill unfused E2 cells) (11). Colonies appearing after two weeks of growth were expanded and RNA and DNA prepared for analysis. From a single fusion experiment, an average of 36 hybrid clones were obtained (range of 17 to 80 in five different individuals).

Figure 2A:
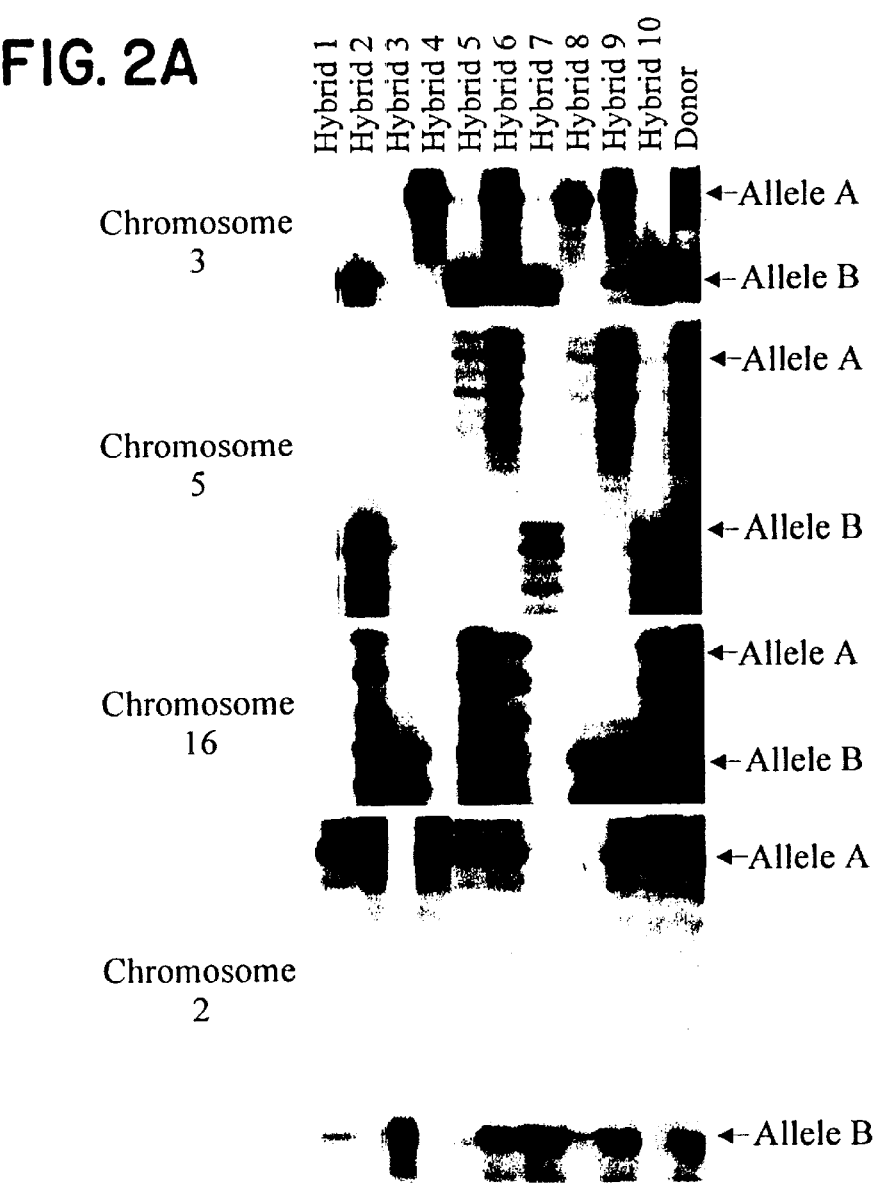
FIGS. 2A to 2B. Allelic status and gene expression in hybrids.

All hybrids contained the human X chromosome, as this chromosome contains the HPRT gene allowing growth in HAT. To determine whether other human chromosomes were present in the hybrids, polymorphic microsatellite markers (12) were used as probes in PCR-based assays (FIG. 2A). We focused on the chromosome arms (2p, 2q, 3p, 5q, 7q, and 16q) known to contain colorectal cancer (CRC) predisposition genes. One copy of each of these chromosome arms was present in a significant fraction of the hybrid clones. For example, of 476 hybrids derived from 14 individuals and examined for chromosome 3, 136 hybrids contained neither donor chromosome, 211 hybrids contained both donor chromosomes, 60 hybrids contained one parent's chromosome, and 69 hybrids contained the other parent's chromosome. Similar retention frequencies were found for all six chromosome arms analyzed. Testing of markers from both arms of a single chromosome showed that whole chromosomes, rather than chromosome fragments, were generally retained in the hybrids. This result was confirmed with fluorescence in situ hybridization (FISH) on metaphase spreads from the hybrids, which indicated the presence of 11±3 human chromosomes in each hybrid cell. Calculations based on the genotypic data indicated that the analysis of 25 hybrids would ensure a 95% probability of identifying at least one hybrid containing the maternal allele and one hybrid containing the paternal allele of a single chromosome under study. Moreover, it would require only 45 hybrids to similarly ensure that each allele of all 22 autosomes was present and separated from its homolog in at least one hybrid (13).

Example 2

Figure 2B:
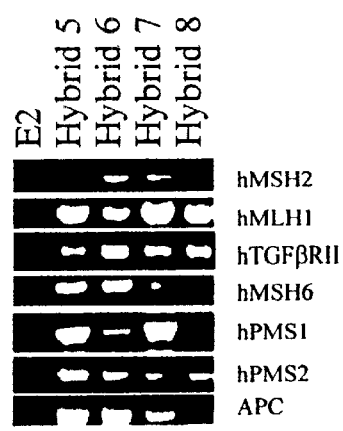
Figure 3A:
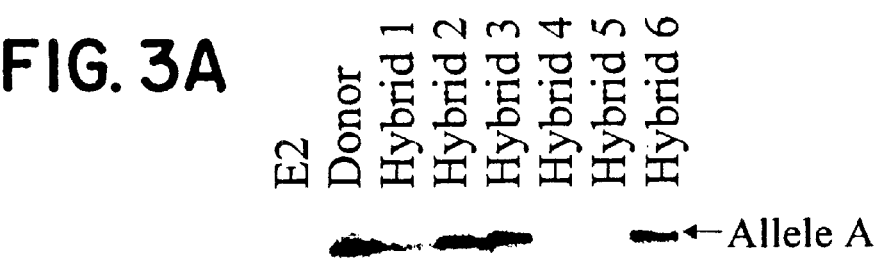
FIGS. 3A to 3C. Mutational analysis of an HNPCC patient refractory to standard genetic diagnosis. Nucleic acids from the indicated hybrids were tested for retention of chromosomes 2 and 3 using polymorphic markers (FIG. 3A) and for expression of hMSH2 and hMLH1 genes on chromosomes 2 and 3, respectively (FIG. 3B). Hybrids 1, 2, 3, and 6 contained allele A from chromosome 2 and did not express hMSH2 transcripts, while hybrids 4 and 5 contained the B allele and expressed hMSH2. hMLH1 expression served as a control for the integrity of the cDNA.
Figure 3B:
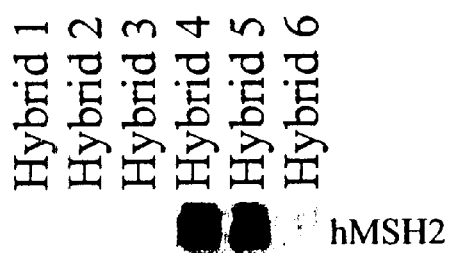
Figure 3B:
Figure 3C:
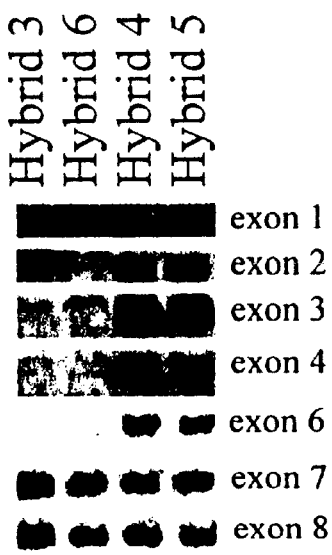

Two other features of the hybrids were essential for the analyses described below. First, the human chromosome complements of the hybrids were remarkably stable. Polymorphic marker analysis in ten hybrids revealed identical patterns of retention after growth for 90 (30 passages) generations after initial genotyping. Second, those hybrids containing the relevant chromosome expressed every human gene assessed, including all known colorectal cancer susceptibility genes (the hMSH2 and hMSH6 genes on chromosome 2p, the hPMS1 gene on chromosome 2q, the TGF-β Receptor Type II gene and hMLH1 gene on chromosome 3p, the APC gene on chromosome 5q, the hPMS2 gene on chromosome 7q, and the E-cadherin gene on chromosome 16q; representative examples in FIG. 2B) (14).

Example 3

Figure 4A:
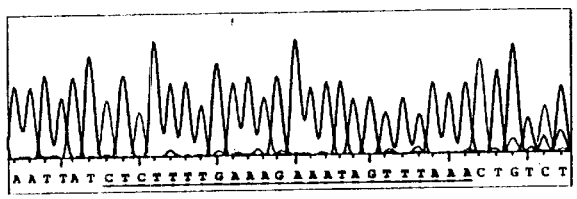
FIGS. 4A to 4C. Mutational analysis of Warthin family G.
Figure 4A:
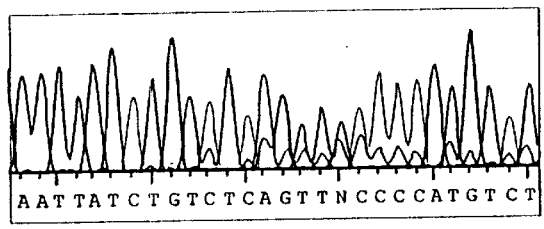
Figure 4A:
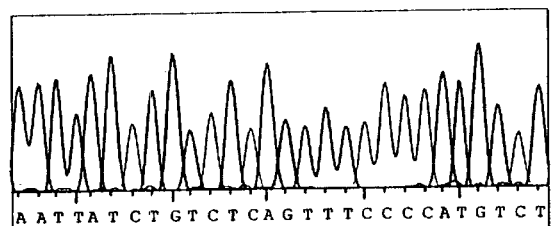
Figure 4B:
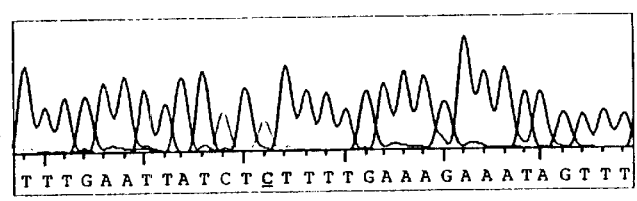
Figure 4B:
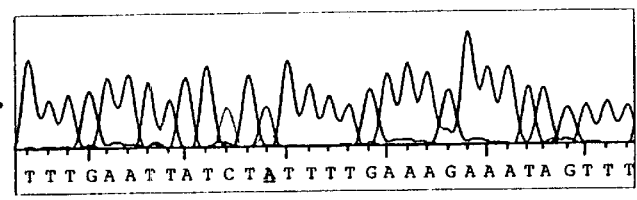
Figure 4B:
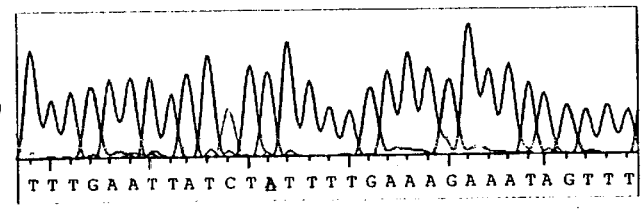
Figure 4C:
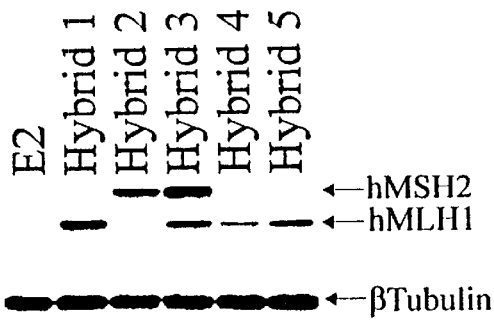

Having established the stability and expression patterns of CRC-predisposition genes in these hybrids, we used this "conversion" approach to investigate ten patients who had proven refractory to standard genetic diagnostic techniques. Each of these patients had a significant family history of colorectal cancer and evidence of mismatch repair deficiency in their tumors, yet sequencing of the entire coding sequence of each known MMR gene had failed to reveal mutations. Indeed, these and similar studies have prompted the speculation that other major HNPCC genes must exist. (25–34) Hybrids were generated from lymphocytes of each patient, and at least one hybrid containing the maternal allele and one hybrid containing the paternal allele of each MMR gene was isolated. Analysis of the nucleic acids from these hybrids revealed specific mutations in all ten patients (Table 1). In every case, an abnormality was found in a single allele of either hMSH2 or hMLH1. The nature of the abnormalities revealed why they had not been detected with the standard methods previously used for their analysis. Three cases were due to large deletions, encompassing six or seven exons. When corresponding nucleic acids from the cells of such patients are evaluated by any PCR-based method, only the wild type sequences from the unaffected parent would be amplified, leading to the false impression of normalcy (for example, case #1 in FIG. 3). Though Southern blotting can reveal deletions of one or a few exons in MMR, larger deletions are refractory to such blotting methods. In three cases (#4, 6, and 9), no transcript was generated from one allele, though the sequences of all exons and intron-exon borders from this allele were normal. Presumably, mutations deep within an intron or within the promoter of the gene were responsible. The absence of transcripts from one specific allele of these three patients was confirmed in at least three other converted hybrids from each patient. In four other cases, point mutations were found (Table 1). These mutations were not detected in the original sequence analyses because the signals from the mutant allele were not as robust as those from the wild type. Such asymmetry can be caused by instability of mutant transcripts due to nonsense mediated decay (36–38), or to nucleotide preferences of the polymerases in specific sequence contexts, and represents a common problem for both manual and automated sequencing methods (39). The conversion approach eliminates these problems because only one sequence can possibly be present at each position. A good example of this was provided by Warthin G (17). The mutation in this prototype kindred was an A to C transversion at a splice site. The signal from the mutant "C" in the sequencing ladder was not as intense as the wild type "A" (FIG. 4b). This mutation led to the use of a cryptic splice site 24 bp upstream of exon 4, and an under-represented transcript with a 24 base insertion (FIG. 4a). To demonstrate that this mutation had an effect at the protein level, we analyzed the hybrids by immunoblotting with specific antibodies (19). The hybrids containing the mutant allele did not make detectable levels of human hMSH2 protein, though they did synthesize normal levels of a control protein (FIG. 4C).

The results described above demonstrate that individual alleles of human chromosomes can be readily isolated upon fusion to mouse cells.

HNPCC provides a cogent demonstration of the power of the conversion approach because it is a common genetic disease that has been widely studied. In the last three years, for example, extensive analyses of the major MMR genes have been performed in 303 HNPCC kindreds from nine cohorts distributed throughout the world (25–34). Based on the fraction of such patients with characteristic microsatellite instability in their cancers (30–34), it can be estimated that 239 (78%) of the kindreds had germ-line mutations of mismatch repair genes. Yet MMR gene mutations were identified in only 127 (42%) of these 239 kindreds (25–34). Our cohort was similar, in that it was derived from a total of 25 kindreds, 22 of whom had tumors with microsatellite instability and presumptive MMR gene mutations. Of these 22, our initial analyses revealed mutations in only 12 (54%) (ref. 14 and unpublished data). Mutations of the other ten patients were only revealed upon conversion analysis, which thereby increased the sensitivity from 54% to 100%. The conclusion that virtually all cases of HNPCC associated with MSI are due to germline mutations of known MMR genes is consistent with recent immunohistochemical data demonstrating the absence of either MSH2 or MLH1 protein staining in the cancers from the great majority of HNPCC patients (40, 41). A corollary of these results is that the search for new human MMR genes should not based on the premise that a large fraction of HNPCC cases will prove attributable to such unknown genes.

The system described above can be applied to other genetic diseases in a straight forward manner. It should be emphasized that this approach is not a substitute for the many powerful methods currently available to search for specific mutations. Rather, conversion can be used to maximize the sensitivity of existing techniques. Converted nucleic acids provide the preferred substrates for such methods because of the higher signal to noise attainable and the inability of the wild type allele to mask or confound detection of the mutant allele. As DNA-based mutational assays are improved in the future, and progressive incorporate microarrays and other automatable features (42–44), the value of conversion-generated nucleic acids will correspondingly increase, significantly enhancing the effectiveness of genetic tests for hereditary disease.

Methods

Cell Culture

Mouse embryonic fibroblasts were derived from MSH2-deficient mice (46) and transformed with adenovirus E1A and RAS oncogenes. HPRT-deficient subclones were selected by growing the fibroblasts in 10 $\mu$M 2-amino-6-mercaptopurine. Clones were maintained in Dulbecco's modified Eagle's Medium (DMEM) supplemented with 10% FCS and 10 $\mu$M 2-amino-6-mercaptopurine. Cell fusion and the generation of hybrids The patients were from kindreds with HNPCC as defined by the Amsterdam criteria (44); in no case was linkage analysis feasible due to the lack of a sufficient number of affected individuals. Microsatellite instability (MSI) in the cancers from these patients was determined through the markers recommended in ref. 45. $3 \times 10^6$ E2 cells and $12 \times 10^6$ lymphocytes cells were mixed, washed, and centrifuged twice in fusion medium (0.25 M D-sorbitol, 0.1 mM calcium acetate, 0.5 mM magnesium acetate, 0.1% Bovine Serum Albumin (BSA), pH 7) and resuspended in 640 µl fusion medium. The solution was pipetted into a cuvette (BTX cuvette electrode 470; BTX, San Diego). Cells were fused using a BTX ELECTROCELL MANIPULATOR™, model ECM200, cell fusion apparatus. The settings that yielded the greatest number of hybrids were: 30V (AC) for 22 seconds, followed by three 300V (DC) pulses of 15 µsec each. The cells from one fusion were plated into three 48-well plates (Costar) in DMEM supplemented with 10% FCS. After 24 hours, the medium was replaced by DMEM supplemented with 10% FCS, 0.5 mg/ml geneticin and 1×HAT (Life Technologies, Gaithersburg, Md.). The medium was changed after a week. Hybrid clones became visible two weeks after fusion and were expanded for another week prior to genotyping. From a single fusion, an average of 23+/−15 hybrid clones were obtained. The lymphocytes used for the experiments described here were derived from Epstein-Barr Virus infection of peripheral blood leukocytes, but it was found that freshly drawn lymphocytes could also be successfully fused and analyzed using identical methods.

Genotyping

Genotyping was performed as described (12). PCR products were separated on 6% denaturing gels and visualized by autoradiography. The microsatellite markers used were D2S1788 and D2S1360, D2S1384, D3S2406, D7S1824, and D16S3095, from chromosome 2p, 2q, 3p, 5q, 7q and 16q, respectively. Fluorescence in situ hybridization was performed as described previously (21).

PCR and Sequencing

Polyadenylated RNA was purified and RT-PCR performed as described previously. Sequencing was performed using ABI BIG DYE TERMINATORS™ nucleic acid chain elongation inhibitors and an ABI 377 automated sequencer. All primers used for amplification and sequencing will be made available through an internet site.

Statistical Analysis

The number of hybrids containing none, both or a single allele of each chromosome tested were consistent with a multinomial distribution. Monte Carlo simulations were used to estimate the number of hybrids required to generate mono-allelic hybrids containing specific numbers of each chromosomes.

TABLE 1

Summary of MMR Gene Mutations Identified by Conversion

| Kindred | Gene | Functional abnormality | Genomic DNA alteration |
|---|---|---|---|
| 1 | MSH2 | No detectable transcript | Deletion of exon 1-exon 6 |
| 2 | MSH2 | R680Ter | CGA to TGA |
| 3 | MSH2 | No detectable transcript | Deletion of exon 1-exon 7 |
| 4 | MLH1 | No detectable transcript | NI* |
| 5 | MSH2 | A636P** | GCA to CCA |
| 6 | MLH1 | No detectable transcript | NI* |
| 7 | MSH2 | R680Ter | CGA to TGA |
| 8 | MSH2 | No detectable transcript | Deletion of exon 1-exon 7 |
| 9 | MLH1 | No detectable transcript | NI* |
| 10 | MSH2 | 24 bp insertion between codons 215 and 216 | TAG to GAG, splice acceptor of exon 4 |

*Genomic alteration not identified despite complete sequencing of all exons and intron-exon borders of the abnormal allele.
**Found in other HNPCC kindreds, but not in 400 normal alleles (ref. 46 and unpublished data); mutant product functionally defective (ref. 46).

References and Notes[1]

All references are explicitly incorporated by reference.

1. D. Ravine, *Journal of Inherited Metabolic Disorders* 22, 503 (1999); R. G. Cotton, *Clin Chem Lab Med* 36, 519 (1998)
2. F. J. Couch and B. L. Weber, in *The Genetic Basis of Human Cancer*, B. Vogestein and K. W. Kinzler, Eds. (McGraw-Hill, New York, 1998), pp. 537–563; K. W. Kinzler, B. Vogelstein, *Cell* 87, 159 (1996).
3. T. P. Drja, E. C. Berson *Invest Ophthalmol Vis Sci* 36:1197 (1995); G. C. Black, I. W. Craig, *Mol Genet Med* 4, 1 (1994); Inglehearn, *Eye* 12, 571 (1998).
4. B. Zoller, P. Garcia de Frutos, A. Hillarp, B. Dahlback, *Haematologica* 84, 59 (1999); H. G. Drexler, *Leukemia* 12, 845 (1998); M. Lawler, *Radiat Oncol Investig* 5, 154 (1997).
5. J. B. Martin, Science 262, 674 (1993); U. Muller, M. B. Graeber, G. Haberhausen, A. Kohler, *J. Neurol Sci* 124, 199 (1994); S. Sorbi, *Aging* (Milano) 5, 417 (1993).
6. C. E. Seidman, J. G. Seidman, *Basic Res Cardiol* 93, 13 (1998); M. T. Keating, M. C. Sanguinetti, *Science* 272, 681 (1996).
7. D. Patterson, D. V. Carnright, *Somatic Cell Genet* 3, 483 (1977); J. Groden, et al., *Cell* 66,589 (1991); J. M. Gabriel et al., *Proc Natl Acad Sci USA* 95, 14857 (1998).
8. N. Papadopoulos, F. S. Leach, K. W. Kinzler, B. Vogelstein, *Nature Genetics* 11, 99 (1995); S. J. Laken et al., *Proc Natl Acad Sci USA* 96, 2322 (1999).
9. H. Harris, *J Cell Sci* 79, 83 (1985); M. J. Anderson, E. J. Stanbridge, *FASEB J* 7, 826(1993).
10. E2 cells were derived from mouse embryonic fibroblasts derived from MSH2-deficient mice (generously provided by T. Mak) and transformed with adenovirus E1A and RAS oncogenes. HPRT-deficient subclones were selected by growing the fibroblasts in 10 µM 2-amino-6-mercaptopurine. Clones were maintained in Dulbecco's modified Eagle's Medium (DMEM) supplemented with 10% FCS and 10 µM 2-amino-6-mercaptopurine.
11. $3 \times 10^6$ lymphocytes cells were mixed, washed, and centrifuged twice in fusion medium (0.25 M D-sorbitol, 0.1 mM calcium acetate, 0.5 mM magnesium acetate, 0.1% Bovine Serum Albumin (BSA), pH 7) and resuspended in 640 µl fusion medium. The solution was pipetted into a cuvette (BTX cuvette electrode 470; BTX, San Diego). Cells were fused using a BTX ELECTROCELL MANIPULATOR™, model ECM200, cell fusion apparatus. The settings that yielded the greatest number of hybrids were: 30V (AC) for 22 seconds, followed by three 300V (DC) pulses of 15 µsec each. The cells from one fusion were plated into three 48-well plates (Costar) in DMEM supplemented with 10% FCS. After 24 hours, the medium was replaced by DMEM supplemented with 10% FCS, 0.5 mg/ml geneticin and 1×HAT (Life Technologies, Gaithersburg, Md.). The medium was changed after a week. Hybrid clones became visible two weeks after fusion and were expanded for another week prior to genotyping. The lymphocytes used for the experiments described here were derived from Epstein-Barr virus infection of peripheral blood leukocytes, but we found that freshly drawn lymphocytes could also be successfully fused and analyzed using identical methods 12. Genotyping was performed as described in F. S. Leach et al., *Cell* 75, 1215 (1993). PCR products were separated on 6% denaturing gels and visualized by autoradiography. The microsatellite markers used were D2S1788, D2S13360, D3S2406, D7S1824, and D16S3095, from chromosomes 2p, 2q, 3p, Sq, and 16q, respectively.
13. The numbers of hybrids containing none, both, or a single allele of each chromosome tested were consistent with a multinomial distribution. Monte Carlo simulations were used to estimate the numbers of hybrids required to generate mono-allelic hybrids containing specific numbers of chromosomes.
14. Polyadenylated RNA was purified and RT-PCR performed as described in B. Liu et al., *Nat Medicine* 2, 169 (1996).
15. C. R. Boland, *Am. J. Dig. Dis* 23, 25s-27s (1978); C. R. Boland, *West J. Med.* 139, 351 (183).
16. C. R. Boland, in *The Genetic Basis of Human Cancer*, B. Vogelstein and K. W. Kinzler, Eds (McGraw-Hill, New York, 1998), pp. 333–346.
17. A. S. Warthin, *Archives of Internal Medicine* 12, 546 (1913; H. T. Lynch and A. J. Krush, *Cancer* 27, 1505 (1971).
18. Sequencing was performed using ABI BIG DYE TERMINATORS™ nucleic acid chain elongation inhibitors and an ABI 377 automated sequencer. All primers used for amplification and sequencing will be made available through a Science internet site.
19. Cytoplasmic extracts of cells hybrids were separated by electrophoresis through SDS-polyacrylamide gels and immunoblotted with antibodies specific for human hMSH2 (#NA26, Calboiochem), human hMLH1 (#13271A, Pharmingen), or β-Tubulin (#N357, Amersham).
20. D. R. Cox, *Cytogenet Cell Genet* 59, 80 (1992); M. A. Walter, D. J. Spillett, P. Thomas, J. Weissenbach, P. N. Goodfellow, *Nat Genet* 7, 22 (1994); R. J. Leach, P. O'Connell, *Adv Genet* 33, 63 (1995).
21. C. Lengauer, K. W. Kinzler, B. Vogelstein, *Nature* 386, 623 (1997).
22. M. Chee et al., *Science* 274, 610 (1996).
23. McDaniel, L. D., Legerski, R., Lehmann, A. R., Friedberg, E. C. & Schultz, R. A. *Hum Mutat* 10, 317–21 (1997)
24. Schultz, R. A., Saxon, P. J., Glover, T. W. & Friedbert, E. C. *Proc Natl Acad Sci USA* 84, 4176–9 (1987).
25. Syngal, S. et al. JAMA 282, 247–53 (1999).
26. Bapat, B. V. et al. *Hum Genet* 104, 167–76 (1999).
27. Wijnen, J. T. et al. *N Engl J Med* 339, 511–8 (1998).
28. Wang, Q. et al. *Hum Genet* 105, 79–85 (1999)
29. Holmberg, M. et al. *Hum Mutat* 11, 482 (1998).
30. Bai, Y. Q. et al. *Int J Cancer* 82, 512–5 (1999).
31. Wijnen, J. Et al. *Am J Hum Genet* 61, 329–35 (1997).
32. Heinimann, K. et al. *Cancer* 85, 2512–8 (1999).
33. De Leon, M. P. et al. *Gut* 45, 32–8 (1999).
34. Lamberti, C. et al. *Gut* 44, 839–43 (1999).
35. Wijnen, J. et al. *Nat Genet* 20, 326–8 (1998).
36. Culbertson, M. R. *Trends Genet* 15, 74–80 (1999).
37. Frischmeyer, P. A. & Dietz, H. C. *Hum Mol Genet* 8, 1893–900 (1999).
38. Ruiz-Echevarria, M. J., Czaplinski, K. & Peltz, S. W. *Trends Biochem Sci* 21, 433–8 (1996).
39. Ahrendt, S. A. et al. *Proc Natl Acad Sci USA* 96 7382–7 (1999).
40. Marcus, V. A. et al. *Am J Surg Pathol* 23 1248–55 (1999).
41. Cawkwell, L. et al. *Gut* 45, 409–15 (1999).
42. Eng, C. & Vijg, *J. Nat Biotechnol* 15, 422–6 (1997).
43. Hacia, J. G. & Collins, F. S. *J Med Genet* 36, 730–6 (1999).
44. Vasen, H. F., Mecklin, J. P., Khan, P. M. & Lynch, H. T. *Anticancer Res* 14 1661–4 (1994).
45. Boland, C. R. et al. *Cancer Res* 58, 5248–57 (1998).
46. Reitmair, A. H. et al. *Nat Genet* 11, 64–70 (1995).

What is claimed is:

1. A population of rodent-human hybrid cells which stably maintain their human chromosome content such that at least 95% of the hybrid cells retain the same human chromosomes after growth for 90 generations.
2. The population of rodent-human hybrid cells of claim 1 wherein at least 97% of the hybrid cells retain the same human chromosomes.
3. A population of rodent-human hybrid cells which stably maintain their human chromosome content such that at least 99% of the hybrid cells contain the same human chromosomes.
4. A population of rodent-human hybrid cells which stably maintain their human chromosome content such that at least 99% of the hybrid cells retain the same human chromosomes alter growth for 90 generations.
5. The population of hybrid cells of claim 1 wherein the human chromosome content comprises at least 5 human autosomes.
6. The population of hybrid cells of claim 2 wherein the human chromosome content comprises at least 5 human autosomes.
7. The population of hybrid cells of claim 3 wherein the human chromosome content comprises at least 5 human autosomes.
8. The population of hybrid cells of claim 4 wherein the human chromosome content comprises at least 5 human autosomes.
9. The population of hybrid cells of claim 1 wherein the human chromosome content comprises at least 10 human autosomes.
10. The population of hybrid cells of claim 2 wherein the human chromosome content comprises at least 10 human autosomes.
11. The population of hybrid cells of claim 3 wherein the human chromosome content comprises at least 10 human autosomes.
12. The population of hybrid cells of claim 4 wherein the human chromosome content comprises at least 10 human autosomes.
13. The population of hybrid cells of claim 1 wherein human chromosomes are retained which were not subject to selection.
14. The population of hybrid cells of claim 2 wherein human chromosomes are retained which were not subject to selection.
15. The population of hybrid cells of claim 3 wherein human chromosomes are retained which were not subject to selection.
16. The population of hybrid cells of claim 4 wherein human chromosomes are retained which were not subject to selection.

* * * * *

UNITED STATES PATENT AND TRADEMARK OFFICE
CERTIFICATE OF CORRECTION

PATENT NO. : 6,399,374 B1
DATED : June 4, 2002
INVENTOR(S) : Bert Vogelstein et al.

It is certified that error appears in the above-identified patent and that said Letters Patent is hereby corrected as shown below:

Column 12,
Line 28, "alter" has been replaced with -- after --.

Signed and Sealed this

Eighteenth Day of February, 2003

JAMES E. ROGAN
*Director of the United States Patent and Trademark Office*